(12) United States Patent
Gardiner

(10) Patent No.: US 6,201,014 B1
(45) Date of Patent: Mar. 13, 2001

(54) THERAPEUTICALLY ACTIVE COMPOSITIONS

(75) Inventor: Fiona Kate Gardiner, Beverley (GB)

(73) Assignee: Reckitt & Colman Products Limited, Windsor (GB)

( * ) Notice: Subject to any disclaimer, the term of this patent is extended or adjusted under 35 U.S.C. 154(b) by 0 days.

(21) Appl. No.: 09/445,514

(22) PCT Filed: Jun. 8, 1998

(86) PCT No.: PCT/GB98/01673

§ 371 Date: Dec. 7, 1999

§ 102(e) Date: Dec. 7, 1999

(87) PCT Pub. No.: WO98/56356

PCT Pub. Date: Dec. 17, 1998

(30) Foreign Application Priority Data

Jun. 10, 1997 (GB) .................................................. 9711962

(51) Int. Cl.[7] .......................... A61K 31/335; A61K 31/16
(52) U.S. Cl. ............................................ 514/463; 514/627
(58) Field of Search ...................................... 514/627, 463

(56) References Cited

U.S. PATENT DOCUMENTS

| | | | |
|---|---|---|---|
| 5,063,060 | 11/1991 | Bernstein | 424/422 |
| 5,403,868 | 4/1995 | Reid et al. | 514/586 |
| 5,431,914 | 7/1995 | Adekunle et al. | 424/401 |

FOREIGN PATENT DOCUMENTS

| | | | |
|---|---|---|---|
| 41 37 540 A1 | 5/1993 | (DE) | A61K/35/78 |
| 0 015 334 A1 | 9/1980 | (EP) | A61K/9/02 |
| 2.207.705 | 6/1974 | (FR) | A61K/27/00 |
| WO93/23061 | 11/1993 | (WO) | A61K/35/78 |
| WO6/40079 | 12/1996 | (WO) | A61K/9/24 |
| WO97/03674 | 2/1997 | (WO) | A61K/31/445 |

OTHER PUBLICATIONS

Copy of PCT International Search Report for PCT/GB98/01673 dated Sep. 24, 1998.

*Primary Examiner*—Raymond Henley, III
(74) *Attorney, Agent, or Firm*—Fish & Richardson P.C.

(57) ABSTRACT

A pharmaceutical composition for the treatment of irritable bowel syndrome, diarrhoea, constipation, abdominal pain and/or bloating or abdominal distension, the composition including a carrier vehicle and a vanilloid compound. The carrier vehicle enables the vanilloid compound to be released in the lower gastrointestinal tract. The vanilloid compound has the effect of desensitizing nerves in the lower gastrointestinal tract, thereby leading to symptomatic relief. Preferred vanilloid compounds are capsaicin and resiniferatoxin.

19 Claims, No Drawings

1

THERAPEUTICALLY ACTIVE COMPOSITIONS

This is a 371 of PCT/GB98/01673 filed Jun. 8, 1998.

The present invention relates to compositions for the treatment of irritable bowel syndrome (IBS) and more particularly to locally acting compositions which are active in the post-stomach region of the gastro-intestinal (GI) tract.

BACKGROUND OF THE INVENTION

Irritable Bowel Syndrome (IBS) is part of a spectrum of diseases known generally as Functional Gastrointestinal Disorders which include diseases such as non-cardiac chest pain, non-ulcer dyspepsia, and chronic constipation or diarrhoea. These diseases are all characterised by chronic or recurrent gastrointestinal symptoms for which no structural or biochemical cause can be found. Irritable bowel syndrome in the UK alone is responsible for 30–50% of all gastroenterology referrals to secondary care.

IBS is believed to be due to a number of factors such as physiological, emotional, cognitive and behavioural factors and is frequently encountered during periods of stress. Diagnosis of IBS is one of exclusion and is based on the observed symptoms in any given case. Commonly accepted criteria for IBS, known as the "Rome" criteria, include at least 3 months of continuous or recurrent symptoms of:

1. abdominal pain or discomfort that is relieved with defecation, and/or associated with a change in the frequency of stools, and/or associated with a change in the consistency of stool; and
2. two or more of the following on at least a quarter of occasions: altered stool frequency, altered stool form, altered stool passage, passage of mucus, and/or bloating or feeling of abdominal distension.

Conventional treatments of IBS are based on the severity and the nature of each person's symptoms and whether or not any psychological factors are involved. Treatment of IBS may include one or more of the following: lifestyle changes, pharmacological treatment and psychological treatment. However, there is no general treatment which is applicable to all cases of IBS.

In certain cases, the exclusion of foods which aggravate IBS symptoms is recommended. However, this type of treatment is only effective when the underlying cause of IBS is related to diet.

Pharmacologically active agents are often used to treat IBS. Anti-diarrhoeals (for example, loperamide), smooth muscle relaxants (for example, mebeverine hydrochloride or alverine citrate), or antidepressants may be effective in treating IBS. However, there is no single pharmacologically active agent which is completely effective in alleviating the symptoms or curing TBS.

Psychological factors may be used in the treatment of IBS. Again, however, this treatment does not provide a universal cure for the symptoms of IBS since not all cases of IBS are due to psychological factors.

One method of treating pathological conditions of the small and large intestines is disclosed in U.S. Pat. No. 5,431,914. This patent discloses that the external application of capsaicin to the skin in specific regions affects certain nerves in the skin which lead to spinal cord segments. Thus, it is suggested that topical application of a dose of 0.03 mg capsaicin to the anterior and posterior divisions of spinal nerves T12 to S3 can be used to treat IBS. However, a clear mechanism of the mode of operation of this invention is not known.

Such a regime of self-administration is unlikely to be effective because the composition must be applied to a specific site which is not necessarily readily apparent to the patient. In addition, it is likely to be difficult to control the dosage when applying the composition of U.S. Pat. No. 5,431,914 since it is in the form of a topical cream.

A need therefore exists for a composition which is able to relieve the symptoms of irritable bowel syndrome which ideally is in a form which is easily handled, may be administered in a unit dosage form and which is capable of being self administered by patients.

SUMMARY OF THE INVENTION

To alleviate the problems of IBS, according to a first aspect to the present invention, there is provided a pharmaceutical composition for use in the treatment of irritable bowel syndrome, diarrhoea, constipation, abdominal pain and/or bloating or abdominal distension in a mammal, preferably a human patient, the composition comprising:

i) one or more vanilloid compounds, pharmaceutically acceptable salts, analogues and/or derivatives thereof, (component a); and ii) a pharmaceutically acceptable vehicle (component b), wherein component b) is selected to enable component a) to be released in the gastrointestinal tract between the stomach and the rectum of the mammal.

Preferably component a) is present in a IBS symptom alleviating amount.

Preferably the composition according to the invention contains from 0.001 to 30% of component a), more preferably from 0.01 to 20%, most preferably from 0.1 to 10% by weight of the pharmaceutical composition.

Preferably the composition according to the invention contains from 70 to 99.999% component b), more preferably from 80 to 99.99%, most preferably from 90 to 99.9% by weight of the composition.

According to a second aspect of the invention, there is provided a pharmaceutical composition as described above with respect to the first aspect of the invention, but which further includes an enteric coating (component c) encasing components (a) and (b).

According to a third aspect of the invention, there is provided a process for the alleviation of symptoms associated with Irritable Bowel Syndrome (IBS) in a mammalian patient, preferably a human patient, afflicted with said symptoms, which process comprises the step of:

administering, preferably orally administrating, a therapeutically effective amount of the pharmaceutical composition according to either the first, or second aspects of the invention as described above, in order to alleviate said symptoms associated with Irritable Bowel Syndrome (IBS).

According to a fourth aspect of the invention, there is provided the process according to the third aspect of the invention as described above, wherein the pharmaceutical composition is in a sustained release form, which form is substantially released (i.e., at least 75% of component (a) in the pharmaceutical composition) in the gastrointestinal region after the stomach and before the rectum of the patient being treated.

DETAILED DISCLOSURE

In the context of the present invention, component a) should be understood to be a compound or a mixture of compounds having a biologically active vanillyl group. Component a) therefore includes both naturally occurring and synthetic vanilloids, pharmaceutically acceptable salts of the vanilloid compound (whether natural or synthetic) as well as pharmaceutically acceptable derivatives and/or analogues thereof (whether natural or synthetic).

Included in the ambit of the naturally occurring vanilloid compounds are both crude extracts and purified extracts of active vanilloid compounds.

Examples of natural vanilloid compounds suitable for use in the present invention therefore include both the crude extracts and the purified extracts of active vanilloid compounds from: capsicum, cayenne pepper, black pepper, paprika, cinnamon, clove, mace, mustard, ginger, turmeric, papaya seed and the cactus-like plant *Euphorbia resinifera*.

Synthetic vanilloid compounds such as synthetic capsaicin as defined in WO 96/40079 are also envisaged to be included in or comprise component a) in the compositions of the present invention and the disclosure of such compounds as exemplified in WO 96/40079 is incorporated herein by reference.

The composition of the present invention may therefore include both a crude vanilloid compound-containing extract (obtained by extracting the natural product) and/or a pure vanilloid compound itself (obtained either by synthesis or by refining a crude extract). Thus, in the case of capsaicin, for example, one might also find dihydrocapsaicin present in the crude extract.

In so far as the pharmaceutically acceptable salts of component a) are concerned, the therapeutic activity resides in the moiety derived from the vanilloid, and identity of any salt portion when present is of minor importance.

For therapeutic and prophylactic purposes, examples of pharmaceutically acceptable salts include those derived from mineral acids, such as hydrochloric, hydrobromic, phosphoric, metaphosphoric, nitric and sulphuric acids, and organic acids, such as tartaric, acetic, trifluoroacetic, citric, malic, lactic, fumaric, benzoic, glycollic, gluconic, succinic and methanesulphonic and arylsulphcnic, for example p-toluenesulphonic acids.

In a preferred embodiment of the present invention active vanilloid compounds of component a) are selected from capsaicin ((E)-(N)-[(4-hydroxy-3-methoxyphenyl)-methyl]-8-me thyl-6-nonenamide); eugenol (2-methoxy-4-(2-propenyl)phenol); zingerone (4-(4-hydroxy-3-methoxyphenyl)-2-butanone); curcumin (1,7-bis(4-hydroxy-3-methoxyphenyl)-1,6-heptadiene-3,5-dione); piperine (1-[5-(1,3-benzodioxol-5-yl)-1-oxo-2,4-pentadienyl] piperidine); resiniferatoxin (6,7-deepoxy-6,7-didehydro-5-deoxy-21-dephenyl-21-(phenylmethyl)-20-(4-hydroxy-3-methoxybenzeneaceta te)) or pharmaceutically effective salts, analogues, derivatives or equivalents thereof. Capsaicin, eugenol and resiniferatoxin are more preferred with capsaicin being most preferred.

Component b) of the present invention may comprise and/or include one or more pharmaceutically acceptable excipients or diluents. Such excipients or diluents include but are not limited to mixtures of polyalcohol glycerol and fatty acid esters such as Gelucire (TM of Gattefosse), a carbomer such as Carbopol 947P (TM of Goodrich), calcium carbonate, microcrystalline cellulose, sodium bicarbonate, lactose, croscarmellose sodium, magnesium stearate, talc, dioctyl sodium sulphosuccinate, hydroxypropylmethyl cellulose, methyl paraben, tris (hydroxymethyl) methylamine, citric acid monohydrate, cocoa butter, gelatin, glycerin and/or hydrogenated vegetable oils.

Preferably the composition is an oral delivery form. A composition according to one embodiment of the present invention is therefore preferably administered orally in a sustained-release form to release component a) in the lower GI tract to induce desensitisation, thereby protecting the patient from pain or discomfort associated with the lower GI tract.

The composition may be provided in unit dosage form as a tablet, a capsule, a gel, a powder, spheroids and/or granules. In an especially advantageous embodiment, the composition is provided as a tablet, capsule, spheroid or granule provided with an enteric coating.

Preferably, the excipients and/or diluents are present in an amount of from 0.1 mg to 1500 mg, most preferably from 10 mg to 100 mg per unit dosage form.

Preferably a tablet unit dosage form comprises:
i) 0.01 to 300 mg of component a);
ii) any one or more of
   0.1 to 500 mg microcrystalline cellulose;
   0.1 to 200 mg lactose or equivalent sugar;
   0.1 to 90 mg croscarmellose salt, preferably croscarmellose sodium;
   0.1 to 20 mg of a stearate salt, preferably magnesium stearate; and
iii) an enteric coating of from 1 to 500 μm, all weights being per 1000 mg of composition.

Preferably a capsule unit dosage form comprises:
i) 0.01 to 300 mg component a);
ii) any one or more of
   0.1 to 250 mg mixture of polyalcohol glycerol and fatty acid esters;
   0.1 to 500 mg microcrystalline cellulose;
   0.1 to 200 mg lactose or equivalent sugar;
   0.1 to 90 mg croscarmellose salt, preferably croscarmellose sodium;
   0.1 to 20 mg talc;
   0.1 to 20 mg of a stearate salt, preferably magnesium stearate; and
iii) an enteric coating of from 1 to 500 μm, all weights being per 1000 mg of composition.

Preferably a gel unit dosage form comprises:
i) 0.01 to 300 mg component a);
ii) at least 0.1 to 999.99 mg of a pharmaceutically acceptable polymer gel; and
iii) water, preferably deionised water, all weights being per 1000 mg of composition.

Preferably a powder unit dosage form comprises:
i) 0.01 to 300 mg component a); and
ii) any one or more of
   0.1 to 200 mg of a carbonate, preferably calcium carbonate;
   0.1 to 500 mg microcrystalline cellulose; and
   0.1 to 50 mg of a bicarbonate, preferably sodium bicarbonate, all weights being per 1000 mg of composition.

Preferably a spheroid unit dosage form comprises:
i) 0.01 to 300 mg component a); and
ii) any one or more of
   0.1 to 500 mg microcrystalline cellulose;
   0.1 to 200 mg lactose or equivalent sugar;
   0.1 to 90 mg a croscarmellose salt, preferably croscarmellose sodium; and
iii) an enteric coating of from 1 to 50m, all weights being per 1000 mg of composition.

Preferably a granule unit dosage form comprises:
i) 0.01 to 300 mg component a); and
ii) any one or more of
   0.1 to 200 mg Carbopol;

0.1 to 200 mg of a carbonate, preferably calcium carbonate;

0.1 to 500 mg microcrystalline cellulose; and 0.1 to 50 mg of a bicarbonate, preferably sodium bicarbonate, all weights being per 1000 mg of composition.

The capsules or spheroids may be liquid- or solid-filled. The important feature is that the mode of delivery enables release, preferably sustained release, of component a) in the lower GI tract. Other suitable delivery forms such as matrix tablets and wax matrices will therefore be apparent to the skilled person.

Preferably, each unit dosage contains from 0.01 to 300 mg, preferably 0.1 to 25 mg, most preferably 1 to 20 mg of component a) per 1000 mg of composition.

The amount of component a) required will depend on the particular vanilloid compound used, the severity of the condition being treated, the nature of the oral composition, and the age, weight and condition of the patient.

The dosage administered may ultimately be at the discretion of an attendant physician or may be within a pre-defined range for self-administration by the patient. However, an effective amount of component a) for the treatment of IBS will generally be in the range of 0.01 mg to 40 mg per day and more usually will be in the range of 0.1 mg to 10 mg per day. This amount may be given in a single dose per day or more usually in a number (such as two, three, four, five or six) of sub-doses per day such that the total daily dose is as noted previously.

The amount of component a) contained in the composition will, of course, depend on component b) as well as on the particular vanilloid compound(s) included in component a). For example, capsaicin is much more effective than eugenol and thus the dosage of capsaicin which is needed to achieve the same effect as a dosage of another vanilloid compound, such as eugenol, may be 10 or 100 times smaller.

An effective amount of component a) in the case in which the vanilloid compound is present as a salt may be determined as a proportion of the effective amount of the free active vanilloid compound per se.

As mentioned previously the composition may be enterically coated to provide release of component a) in the gastrointestinal tract between the stomach and the rectum. The enteric coating applied to the unit dosage form may range in thickness form between 1 and 500 μm, preferably between 5 and 100 μm, most preferably between 20 and 50 μm.

A suitable enteric coating comprises pH sensitive biodegradable polymers, as, for example, included in Opadry Aqueous Enteric, manufactured by Colorcon.

It will be appreciated, however, that other release mechanisms for cost stomach (enteric) delivery of component a) may be used, for example, non-pH sensitive biodegradable polymers, or other materials useful for enteric delivery as known in the art.

Alternatively, or in conjunction with the above, the composition may be rectally delivered to the mammal, for example by way of an enema formulation or a suppository.

Preferably an enema formulation contains:

i) 0.01 to 300 percentage weight per volume (% w/v) component a); and ii) any one or more of 0.01 to 10% w/v Dioctyl sulphosuccinate salt, preferably Dioctyl sodium sulphosuccinate;

0.01 to 10% w/v Hydroxypropylmethylcellulose(HPMC);

0.001 to 10% w/v Methyl paraben;

0.001 to 10% w/v Tris(hydroxymethyl)methylamine;

0.001 to 10% w/v Citric acid monohydrate; and iii) the balance being water, preferably deionised water.

Preferably a suppository contains:

i) 0.01 to 300 mg component a); and ii) any one or more of 0.1 to 999.99 mg cocoa butter, gelatin, glycerin and/or hydrogenated vegetable oils; and iii) the balance being water, preferably deionised water all weights being per 1000 mg composition.

According to a further aspect to the present invention, there is provided the use of one or more vanilloid compounds, pharmaceutically acceptable salts, analogues and/or derivatives thereof in the treatment of irritable bowel syndrome, diarrhoea, constipation, abdominal pain and/or bloating or abdominal distension in a mammal, said use comprising releasing a therapeutically effective amount of the vanilloid compound(s), pharmaceutically acceptable salts, analogues and/or derivatives thereof in the gastrointestinal tract between the stomach and the rectum of the mammal.

According to a further aspect to the present invention, there is provided the use of one or more vanilloid compounds, pharmaceutically acceptable salts, analogues and/or derivatives thereof for the manufacture of a medicament for the treatment of irritable bowel syndrome, diarrhoea, constipation, abdominal pain and/or bloating or abdominal distension in a mammal, wherein the one or more vanilloid compounds, pharmaceutically acceptable salts, analogues and/or derivatives thereof are released in the gastrointestinal tract between the stomach and the rectum of the mammal.

A further aspect to the present invention provides a method of treating the treatment of irritable bowel syndrome, diarrhoea, constipation, abdominal pain and/or bloating or abdominal distension in a mammal, the method comprising administering to a mammal in need thereof, a therapeutically effective amount of a pharmaceutical composition comprising i) one or more vanilloid compounds, pharmaceutically acceptable salts, analogues and/or derivatives thereof (component a); and ii) a pharmaceutically acceptable vehicle (component b), wherein component b) is selected to enable component a) to be released in the gastrointestinal tract between the stomach and the rectum of the mammal.

A further aspect to the present invention provides a process for the manufacture of a composition according to the invention, the process including the steps of mixing component a) with component b).

It will be appreciated that the compositions may be prepared by any method known in the art of pharmacy, for example by bringing into association component a) with component b), and excipient(s) and/or diluents when present.

Each of the materials described in this specification are commercially available from various sources.

The following examples illustrate compositions according to the invention.

EXAMPLE 1
Hard gelatin capsule
The capsule contains:

| | |
|---|---|
| Capsaicin | 10 mg |
| Gelucire (™ of Gattefosse) 53/10 | 90 mg |

The ingredients are melted by heating to around 65°–75° C. and the capsule is filled with a 100 mg amount of the melt, which is then allowed to solidify. The capsules are coated with an enteric coating to provide release in the intestine. Gelucire (TM of Gattefosse) consists of mixtures of polyalcohol glycerol and fatty acid esters and the capsaicin is thus dispersed in this lipophilic material.

EXAMPLE 2
Bioadhesive granule

Each capsule contains 10 mg of capsaicin in granular form. The granules are formed of the following ingredients (the weight given for each ingredient being that required to provide sufficient granules to achieve the desired dosage per capsule):

| | |
|---|---|
| Capsaicin | 10 mg |
| Carbopol 947P (™ of Goodrich) | 80 mg |
| Calcium carbonate | 80 mg |
| Microcrystalline cellulose | 200 mg |
| Sodium bicarbonate | 15 mg |

The carbopol, calcium carbonate and microcrystalline cellulose in the form of dry powders are mixed in a high speed food processor. The capsaicin is dissolved in isopropanol and mixed with the resulting powder mixture. The solvent is then dried off at 20° C., sodium bicarbonate is added in powder form and mixed with the dry mass. The resulting mixture is granulated with water and dried at 40° C. in a fluid bed drier to a moisture content of less than 5% w/w. The granules are filled into size one hard gelatin capsules which are then coated with enteric coating polymer.

EXAMPLE 3
Enteric-coated Tablet

| | |
|---|---|
| Capsaicin | 10 mg |
| Microcrystalline Cellulose | 172 mg |
| Lactose | 85 mg |
| Croscarmellose Sodium | 30 mg |
| Magnesium Stearate | 3 mg |

The ingredients are blended and compressed directly into tablets. The tablets are coated with an enteric coating to ensure that capsaicin is released after passing through the stomach. An example of such an enteric coating is Opadry Aqueous Enteric (manufactured by Colorcon).

EXAMPLE 4
Hard Gelatin Capsule

| | |
|---|---|
| Capsaicin | 10 mg |
| Microcrystalline Cellulose | 170 mg |
| Lactose | 85.5 mg |
| Croscarmellose Sodium | 30 mg |
| Talc | 3 mg |
| Magnesium Stearate | 1.5 mg |

The ingredients are blended and filled into hard gelatin capsules (for example, size 2). The capsules are then coated with an enteric coating, for example with Opadry Aqueous Enteric.

EXAMPLE 5
Extrusion Spheronised Pellets in a Hard Gelatin Capsule

| | |
|---|---|
| Capsaicin | 10 mg |
| Microcrystalline Cellulose | 130 mg |
| Lactose | 130 mg |
| Croscarmellose Sodium | 15 mg |

The powders are blended together and then wet massed in a high-shear mixer/granulator. The mass is extruded through a screen (for example, 1 mm) and then spheronised. The spheroids are dried in a fluid-bed dryer and then coated with an enteric coat, for example Opadry Aqueous Enteric. The coated spheroids are filled into hard gelatin capsules (for example, size 2).

EXAMPLE 6
Hard gelatin capsule

| The capsule contains: | |
|---|---|
| Resiniferatoxin | 10 mg |
| Gelucire (™ of Gattefosse) 53/10 | 90 mg |

The ingredients are melted by heating to around 65°–75° C. and the capsule is filled with a 100 mg of the melt, which is then allowed to solidify. The capsules are coated with an enteric coating to provide release in the intestine. Gelucire (TM of Gattefosse) consists of mixtures of polyalcohol glycerol and fatty acid esters and the capsaicin is thus dispersed in this lipophilic material.

EXAMPLE 7
Foam enema

| The enema formulation contains: | |
|---|---|
| Ingredient | % wt/v |
| Eugenol | 0.15 |
| Dioctyl sodium sulphosuccinate | 1.0 |
| Hydroxypropylmethylcellulose (HPMC) | 1.3 |
| Methyl paraben | 0.15 |
| Tris(hydroxymethyl)methylamine | 0.15 |
| Citric acid monohydrate | 0.08 |
| Deionised water | to 100 ml |

The citric acid, tris and methyl paraben are dissolved in 50 ml of deionised water and stirred. HPMC is added to this solution to give solution A. Dioctyl sodium sulphosuccinate is dissolved separately in 25 ml deionised water and the eugenol added to the solution to give solution B. Solutions A and B are carefully mixed to avoid foaming and made to up to 100 ml with deionised water.

EXAMPLE 8

Suppository

| Each supposity contains: | |
|---|---|
| Capsaicin | 10 mg |
| Gelatin | 200 mg |
| Glycerin | 700 mg |
| Deionised water: | 90 mg |

The amounts illustrated above are understood to be per suppository and should therefore be multiplied by the number of suppositories it is expected each production batch will yield.

The ingredients are mixed together and melted at between 60° and 70° C. The melted mass is poured into disposable moulds of plastic material in which the suppositories are cast and remain enclosed until removed by the patient.

EXAMPLE 9

Treatment of IBS in a human patient

A human patient suffering from one or more of the following symptoms: diarrhoea, constipation, abdominal pain, abdominal bloating, abdominal distension, altered stool frequency, altered stool form, altered stool passage or passage of mucus (symptoms associated with Irritable Bowel Syndrome (IBS) is administered a therapeutically effective amount of the pharmaceutical composition according to any of Examples 1 to 8 by either oral or rectal administration, wherein the pharmaceutical composition is administered with sufficient frequency (one administration of the pharmaceutical composition, or multiple administrations of the pharmaceutical composition) in order to alleviate one or more of the symptoms in the said patient.

What is claimed is:

1. A pharmaceutical oral delivery composition for use in the treatment of irritable bowel syndrome, diarrhoea constipation, abdominal pain and/or bloating or abdominal distension in a mammal, said composition being in dosage form as a capsule, a gel, a powder, spheroids or granules and comprising:
   (i) capsaicin or resiniferatoxin, pharmaceutically acceptable salts, analogues and/or derivatives thereof (component (a)); and
   (ii) a pharmaceutically acceptable vehicle (component (b)),
wherein the composition is in unit dosage form as an osmotic delivery device or is enterically coated to provide release of component (a) in the gastrointestinal tract between the stomach and the rectum of the mammal and component (b) is selected to enable component (a) to be released in the gastrointestinal tract between the stomach and the rectum of the mammal.

2. A pharmaceutical oral delivery composition for use in the treatment of irritable bowel syndrome, diarrhoea, constipation, abdominal pain and/or bloating or abdominal distension in a mammal, said composition being in tablet dosage form and comprising:
   (i) capsaicin or resiniferatoxiin, pharmaceutically acceptable salts, analogues and/or derivatives thereof (component (a)), and
   (ii) a pharmaceutically acceptable vehicle (component (b)),
wherein the composition is in unit dosage form as an osmotic delivery device to provide release of component (a) in the gastrointestinal tract between the stomach and the rectum of the mammal and component (b) is selected to enable component (a) to be released in the gastrointestinal tract between the stomach and the rectum of the mammal.

3. A composition according to claim 1 or 2 wherein component (b) releases component (a) only after the composition has passed through the stomach.

4. A composition according to claim 1 or 2 wherein the unit dosage contains from 0.01 to 300 mg of component (a).

5. A capsule unit dosage form composition for use in the treatment or irritable bowel syndrome, diarrhoea, constipation, abdominal pain and/or bloating or abdominal distension in a mammal, the composition comprising:
   i) from 0.01 to 300 mg of capsaicin or resiniferatoxin, pharmaceutically acceptable salts, analogues and/or derivatives thereof;
   ii) any one or more of
      0.1 to 250 mg of a mixture of polyalcohol glycerol and fatty acid esters,
      0.1 to 500 mg of microcrystalline cellulose,
      0.1 to 200 mg of lactose or equivalent sugar,
      0.1 to 90 mg of croscarmellose salt, preferably croscarmellose sodium,
      0.1 to 20 mg of talc, and
      0.1 to 20 mg of a stearate salt; and
   iii) from 1 to 500 $\mu$m of an enteric coating. all weights being per 1000 mg of composition.

6. A composition according to claim 5 in which the croscarmellose salt is croscarmellose sodium and the stearate salt is magnesium stearate.

7. A gel unit dosage form composition for use in the treatment or irritable bowel syndrome, diarrhoea, constipation, abdominal pain and/or bloating or abdominal distension in a mammal, the composition comprising:
   i) from 0.01 to 300 mg of capsaicin or resiniferatoxin, pharmaceutically acceptable salts, analogues and/or derivatives thereof;
   ii) 0.1 to 999.99 mg of a pharmaceutically acceptable polymer gel; and
   iii) water,
all weights being per 1000 mg of composition.

8. A powder unit dosage form composition for use in the treatment or irritable bowel syndrome, diarrhoea, constipation, abdominal pain and/or bloating or abdominal distension in a mammal, the composition comprising:
   i) from 0.01 to 300 mg of capsaicin or resiniferatoxin, pharmaceutically acceptable salts, analogues and/or derivatives thereof; and
   ii) any one or more of
      0.1 to 200 mg of a carbonate,
      0.1 to 500 mg of microcrystalline cellulose, and
      0.1 to 50 mg of a bicarbonate,
all weights being per 1000 mg of composition.

9. A composition according to claim 8 in which the carbonate is calcium carbonate and the bicarbonate is sodium bicarbonate.

10. A spheroid unit dosage form composition for use in the treatment or irritable bowel syndrome, diarrhoea, constipation, abdominal pain and/or bloating or abdominal distension in a mammal, the composition comprising:
   i) from 0.01 to 300 mg of capsaicin or resiniferatoxin, pharmaceutically acceptable salts, analogues and/or derivatives thereof; and
   ii) any one or more of
      0.1 to 500 mg of microcrystalline cellulose,
      0.1 to 200 mg of lactose or equivalent sugar, and 0.1 to 90 mg of a croscarmellose salt; and iii) from 1 to 500 mg of an enteric coating, all weights being per 1000 mg of composition.

11. A composition according to claim 10 in which the croscarmellose salt is croscarmellulose sodium.

12. A granule unit dosage form composition for use in the treatment or irritable bowel syndrome, diarrhoea, constipation, abdominal pain and/or bloating or abdominal distension in a mammal, the composition comprising:

i) from 0.01 to 300 mg of capsaicin or resiniferatoxin, pharmaceutically acceptable salts, analogues and/or derivatives thereof; and ii) any one or more of 0.1 to 200 mg of a carbomer, 0.1 to 200 mg of a carbonate.

0.1 to 500 mg of microcrystalline cellulose, and 0.1 to 50 mg of a bicarbonate.

all weights being per 1000 mg of composition.

13. A composition according to claim 12 in which the carbonate is calcium carbonate and the bicarbonate is sodium bicarbonate.

14. A composition according to claim 4 wherein the unit dosage contains from 0.1 to 20 mg of component (a).

15. A composition according to claim 1 or 2 in which component (a) is capsaicin.

16. A method for treating irritable bowel syndrome, diarrhoea, constipation, abdominal pain and/or bloating or abdominal distension which comprises administering to a patient in need of such treatment a therapeutically effective amount of capsaicin or resiniferatoxin in a dosage form which causes the capsaicin or resiniferatoxin to be released in the gastrointestinal tract of said patient between the stomach and the rectum.

17. A method according to claim 16 in which the capsaicin or resiniferatoxin is in a unit dosage form as an osmotic delivery device or is enterically coated and comprises a pharmaceutically acceptable vehicle.

18. A method according to claim 17 in which the unit dosage form is a tablet, a capsule, a gel, a powder, spheroids or granules.

19. A method according to claim 17 wherein the unit dosage contains from 0.01 to 300 mg of capsaicin or resiniferatoxin.

* * * * *

UNITED STATES PATENT AND TRADEMARK OFFICE
CERTIFICATE OF CORRECTION

PATENT NO. : 6,201,014 B1
DATED : March 13, 2001
INVENTOR(S) : Fiona Kate Gardiner Page 1 of 1

It is certified that error appears in the above-identified patent and that said Letters Patent is hereby corrected as shown below:

Title page,
Item [56] References Cited, Foreign Patent Documents, delete "WO6/40079" and insert -- WO96/40079 --.

Column 9,
Line 38, after "diarrhoea" insert -- , --.
Line 60, delete "resiniferatoxiin" and insert -- resiniferatoxin --.

Column 11,
Line 2, delete "mg" and insert -- µm --.

Signed and Sealed this

Sixteenth Day of October, 2001

Attest:

NICHOLAS P. GODICI
*Attesting Officer*   *Acting Director of the United States Patent and Trademark Office*